US010695229B2

(12) United States Patent
Toth

(10) Patent No.: US 10,695,229 B2
(45) Date of Patent: Jun. 30, 2020

(54) SELF-SEALING DRESSING

(75) Inventor: Landy Aaron Toth, Newtown, PA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 13/992,646

(22) PCT Filed: Dec. 7, 2011

(86) PCT No.: PCT/US2011/063648
§ 371 (c)(1),
(2), (4) Date: Jul. 26, 2013

(87) PCT Pub. No.: WO2012/078707
PCT Pub. Date: Jun. 14, 2012

(65) Prior Publication Data
US 2013/0296762 A1 Nov. 7, 2013

Related U.S. Application Data

(60) Provisional application No. 61/420,997, filed on Dec. 8, 2010.

(51) Int. Cl.
A61F 13/02 (2006.01)
A61L 15/58 (2006.01)
(Continued)

(52) U.S. Cl.
CPC ...... A61F 13/0253 (2013.01); A61F 13/0216 (2013.01); A61F 13/0243 (2013.01);
(Continued)

(58) Field of Classification Search
CPC .. A61F 13/02; A61F 13/0233; A61F 13/0246; A61F 13/0253; A61M 1/0088
(Continued)

(56) References Cited

U.S. PATENT DOCUMENTS 4,743,499 A * 5/1988 Volke .......................... 428/317.3
4,834,979 A * 5/1989 Gale ....................... A61K 9/703
424/447
(Continued)

FOREIGN PATENT DOCUMENTS

| JP | 2004305594 A | 11/2004 |
| WO | WO-2011136330 A1 | 11/2011 |
| WO | WO 2012/078707 | 6/2012 |

OTHER PUBLICATIONS

PCT/US2011/063648 International Preliminary Report on Patentability dated Jun. 12, 2013.
(Continued)

Primary Examiner — Anna K Kinsaul
Assistant Examiner — Camtu T Nguyen
(74) Attorney, Agent, or Firm — Taft Stettinius & Hollister LLP; Ryan O. White

(57) ABSTRACT

A self-sealing dressing (10) for application to skin of a human may include a substrate (12) including elastomeric material, and a cold flow adhesive layer (18) coupled to the substrate. The adhesive layer (18) may be adapted to adhere to skin of a human to form a substantially gas impermeable seal between the adhesive layer (18) and the skin that is maintained during repeated flexure and/or extension of the dressing. A maximum thickness of the combination of the substrate (12) and the adhesive layer (18) may be about 25 um.

16 Claims, 2 Drawing Sheets

(51) Int. Cl.
*A61L 15/42* (2006.01)
*A61F 13/00* (2006.01)
*A61M 1/00* (2006.01)

(52) U.S. Cl.
CPC ............... *A61L 15/42* (2013.01); *A61L 15/58* (2013.01); *A61F 2013/00536* (2013.01); *A61M 1/0088* (2013.01)

(58) Field of Classification Search
USPC ........................................ 602/42–43, 52, 54
See application file for complete search history.

(56) References Cited

U.S. PATENT DOCUMENTS

| | | | | |
|---|---|---|---|---|
| 5,109,874 | A | * | 5/1992 | Bellingham .......... A61F 15/004 128/888 |
| 5,555,584 | A | * | 9/1996 | Moore, III ............... A43B 7/28 12/142 N |
| 6,191,336 | B1 | * | 2/2001 | Mashiko ............. A61F 13/0276 602/41 |
| 6,479,724 | B1 | * | 11/2002 | Areskoug ............... A61L 15/58 602/41 |
| 6,506,957 | B1 | * | 1/2003 | Himmelsbach ..... A61F 13/0243 602/41 |
| 2001/0029956 | A1 | | 10/2001 | Argenta et al. |
| 2003/0232905 | A1 | * | 12/2003 | Ives ..................... C08K 5/0008 524/35 |
| 2004/0064132 | A1 | * | 4/2004 | Boehringer .......... A61M 1/0011 604/543 |
| 2007/0027423 | A1 | * | 2/2007 | Scheinberg et al. ............ 602/54 |
| 2007/0167926 | A1 | * | 7/2007 | Blott .................... A61F 13/0213 604/304 |
| 2008/0145443 | A1 | * | 6/2008 | Langolf .................... A61K 8/26 424/523 |
| 2010/0159192 | A1 | * | 6/2010 | Cotton .................... A61L 15/42 428/137 |
| 2011/0290259 | A1 | * | 12/2011 | McGuire, Jr. ........... A61L 15/46 128/849 |
| 2014/0242149 | A1 | * | 8/2014 | Gantner ................. C09J 183/06 424/445 |
| 2014/0243727 | A1 | * | 8/2014 | Gibas ...................... B41F 15/00 602/55 |

OTHER PUBLICATIONS

PCT/US2011/063648 Written Opinion dated Mar. 12, 2012.
PCT/US2011/063648 International Search Report dated Mar. 12, 2012.
Chinese Patent Application No. 201180067110.4 Office Action dated Aug. 2, 2016.
European Patent Application No. 11846381.9 Communication dated Jun. 13, 2016.
European Patent Application No. 11846381.9 Communication dated Mar. 21, 2017.
Canadian Patent Application No. 2,819,462 Office Action dated Oct. 26, 2017.

* cited by examiner

SELF-SEALING DRESSING

CROSS-REFERENCE TO RELATED APPLICATION

The present application claims benefit of the filing date of U.S. Provisional Patent Application No. 61/420,997, filed Dec. 8, 2010, entitled "Self-Sealing Dressing", the disclosure of which is hereby incorporated herein by reference.

BACKGROUND OF THE INVENTION

Existing dressings for reduced pressure therapy or negative pressure wound therapy (NPWT) often can be overly stiff and the pressure sensitive adhesives used to maintain them during use can be prone to leak formation. Thus, it is relatively easy to form leaks between a sealant film of the dressing and the patient's skin, across the border of these films. The formation of a leak usually results in an alarm condition that must be reset by an attending nurse or caregiver. Attending to the leaks that arise during NPWT can consume appreciable resources and decrease caregiver efficiency. In addition, leaks can result in reduced efficacy of treatment for the patient.

In the treatment of some wounds, especially those covering pressure bearing areas, such as the feet and sacral region, and those near high use regions of the body, such as hands, dressings can be prone to curling up during use. This is often referred to as rucking. Rucking can lead to catching of the dressing on adjacent objects, loss of seal and/or exposure of the wound site to the surroundings. Generally, the highly aggressive adhesives currently used in reduced pressure therapy may be particularly prone to this phenomenon, as exposed adhesives are more likely to catch on adjacent surfaces.

Furthermore, highly aggressive adhesives can be painful to remove, especially around sensitive areas of the body. Less aggressive adhesives, however, typically have not fared well in terms of maintaining adhesion for a wide segment of the patient population during patient activity, and in a range of climates commonly experienced in clinical settings.

As the miniaturization trend for NPWT devices continues, successful miniaturization may depend, in part, on the integrity of the seal around the wound provided by the dressing. In addition, the electrical power requirements needed to maintain a vacuum at a wound site covered by a dressing in the presence of a leak can be dramatically higher than that needed to maintain a vacuum in a low or zero leakage condition.

Further, moist wound healing generally needs a dressing with a relatively moderate moisture vapor transfer rate (MVTR). A typical rate for eliciting a moist wound healing environment is less than 35 g/m²/hr, with risk of maceration occurring for values less than about 8 g/m²/hr. Yet, in the peripheral tissues such as the hands or feet, there is a need for a relatively high MVTR, such as 50-90 g/m²/hr, to minimize moisture storage at the tissue interface, which can lead to unwanted maceration. In addition, it is generally accepted that to maintain a vacuum with minimal effort, a dressing should have an MVTR that is generally as low as possible. Further complicating the situation, patients may perspire at different rates, with such rates fluctuating throughout the day due to changes in the local environment, the patient's degree of activity, clothing, etc. These competing goals for MVTR of a dressing along with the uncertainty of wound exudate liberation and perspiration further complicate the design of a suitable dressing.

Particular to applications in NPWT, the oxygen transfer rate (OTR) of the adhesive film of a dressing may affect the power required to maintain a vacuum on the wound site. Thus a combination of MVTR and OTR may need to be considered to improve the design of a dressing for such applications.

Therefore, there exists a need for a dressing that provides improved wound healing for NPWT, avoids leak formation between the dressing and the patient, avoids edge lifting, rolling or rucking of the dressing during use, avoids causing pain to a patient during a change of the dressing and minimizes the power needed to maintain a vacuum at a wound site to which the dressing is applied.

BRIEF SUMMARY OF THE INVENTION

In accordance with aspects of the invention, a dressing for application to skin of a human may include a substrate including elastomeric material, and a cold flow adhesive layer coupled to the substrate. The adhesive layer may be adapted to adhere to skin of a human to form a substantially gas impermeable seal between the adhesive layer and the skin that is maintained during at least one of repeated flexure or extension of the dressing. A maximum thickness of the combination of the substrate and the adhesive layer may be about 25 μm.

DETAILED DESCRIPTION

Figure 1:
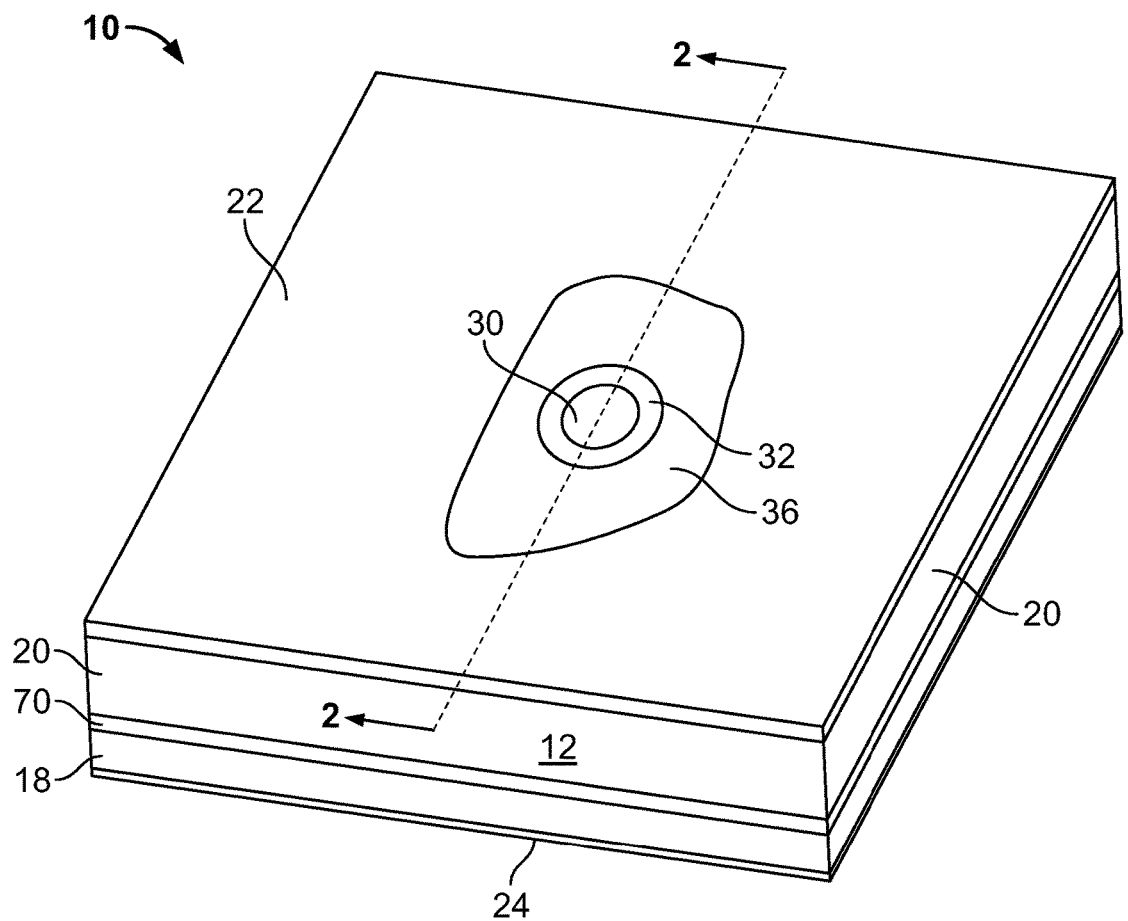
FIG. 1 is a perspective view of a self-sealing dressing, in accordance with an aspect of the invention.
Figure 2:
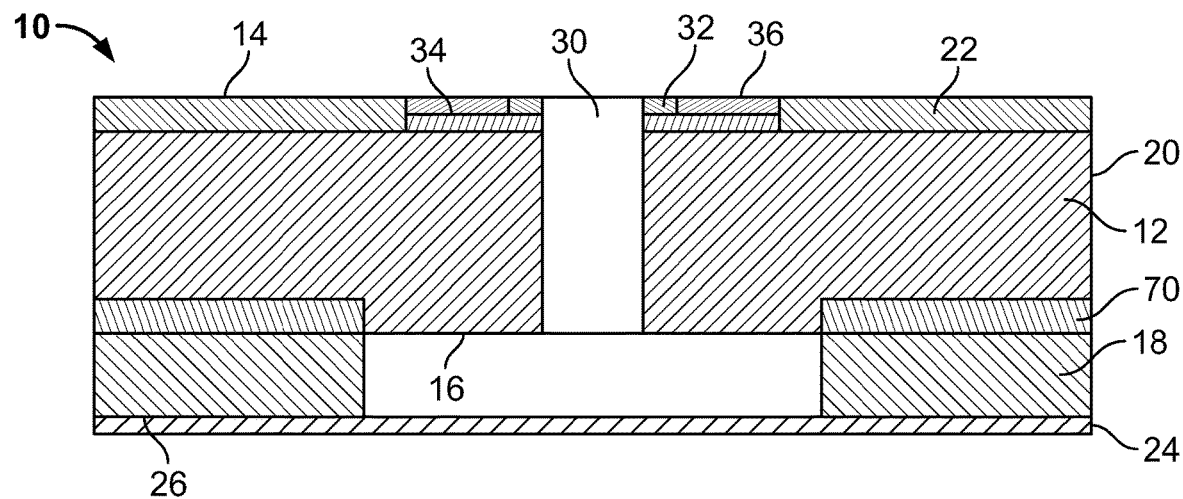
FIG. 2 is a cross-sectional view of the dressing of FIG. 1 taken along line 2-2.

A self-sealing dressing 10 in accordance with aspects of the present invention is shown in FIGS. 1 and 2. The dressing 10 may be in the form of a laminate including a substrate 12 having a top surface 14 and a rear surface 16, and an adhesive layer 18 disposed over a portion of the rear surface of the substrate. The substrate may be a thin polyurethane film and include an elastomer or a thermoplastic elastomer.

As used in this disclosure, terms such as "top", "front", "bottom" and "rear" refer to a frame of reference in which the dressing is applied to a wound site with the rear surface 16 of the substrate facing the wound site. In an applied state of the dressing, the rear surface of the substrate confronts the wound site and the top surface of the substrate faces in a direction away and generally opposite to the wound site.

The adhesive layer may include cold flowing, shear thinning silicone gel adhesive which is patterned along a selected portion or portions of the rear surface 16 of the substrate, such as adjacent to exposed outer edge surfaces 20 of the substrate extending between the top and rear surfaces of the substrate. The adhesive desirably may be formed from biocompatible material and include materials selected so as not to sensitize tissue.

As used in this disclosure, a statement that a surface of a structure of the dressing is "exposed" indicates that the structure is in contact or communication with an environment external to the dressing.

The adhesive layer may be applied on the substrate to have a dry thickness of less than about 50 µm, 25 µm, 10 µm or 5 µm. Generally, for a given composition, the thicker the layer of adhesive, the higher the adhesion strength that can be achieved between the adhesive layer and another surface. In the dressing 10, an adhesive layer having a relatively small thickness may be beneficial for reducing rucking during use.

In one embodiment, the substrate of the dressing may have a thickness of about 1.2-1.9 times greater than the thickness of the adhesive layer. In another embodiment, the substrate and adhesive layer of the dressing may have a combined thickness of at least about 8 µm.

The dressing 10 may include a lubricious layer 22 disposed over the top surface 14 of the substrate 12. The lubricious layer may include materials to render the exposed top surface of the dressing lubricous, decrease the surface energy at the exposed top surface of the dressing, render the exposed top surface of the dressing hydrophobic, and/or decrease the coefficient of friction at the exposed top surface of the dressing.

The dressing 10 also may include a release film layer 24 disposed on a rear surface 26 of the adhesive layer 18 and extending over the rear surface 16 of the substrate. In one embodiment, the release film layer 24 may be disposed along the perimeter of the dressing, only upon the rear surface of the adhesive layer. The release film layer 24 may maintain the adhesive layer in a desired condition during storage and shipping, to prevent flow of the adhesive during shipment and storage. When the dressing is to be applied to a wound site, the dressing may be released from the release layer 24 and placed onto the wound site before significant cold flow of the adhesive gel of the adhesive layer may occur.

The dressing 10 may further include an opening or perforated region 30 extending through the entirety of the thickness of the substrate and which is exposed at the top and rear surfaces of the substrate. A channel or tube fitting 32 may be mounted at the top surface of the substrate to surround the opening 30, using a layer of adhesive 34. The adhesive 34 may be a standard pressure sensitive adhesive. In an alternative embodiment, the adhesive may be a cold flowing silicone gel adhesive, such that self-sealing may occur if the seal is disturbed by patient movement and leaks may be prevented at the point where the suction line is attached to the dressing.

In addition, a foam filled element 36 may be mounted at the top surface of the substrate to surround the channel fitting 32, also using the adhesive layer 34. The foam filled element 36 may be close celled polyurethane foam to minimize leakage while providing a cushioning effect between the wound and the channel fitting.

Figure 3:
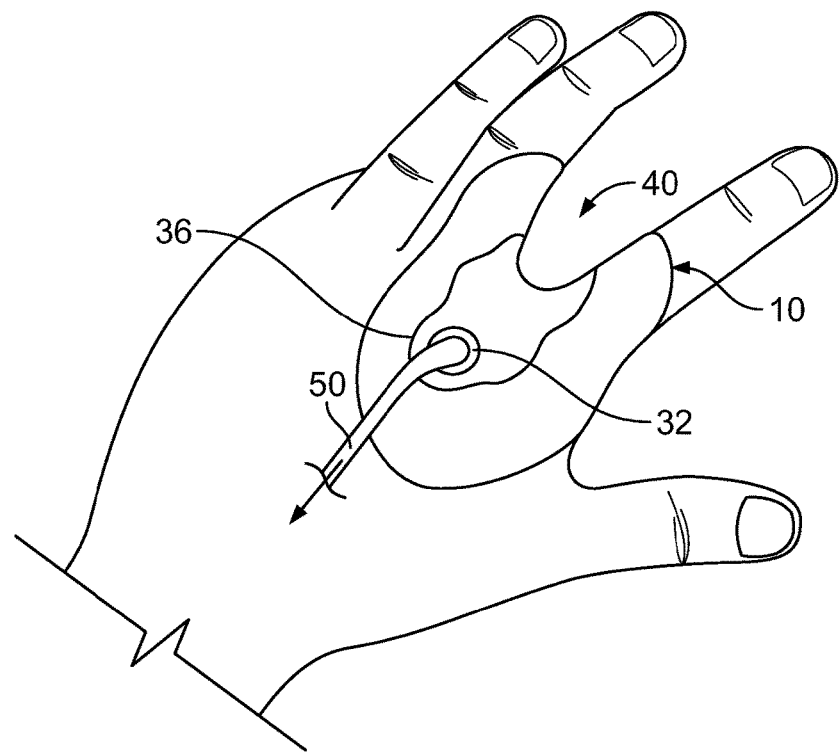
FIG. 3 is a diagrammatic view of a wound site to which an exemplary embodiment of a self-sealing dressing is applied, in accordance with an aspect of the present invention.

In an exemplary application of the dressing 10, the dressing 10 may be used to cover a wound site of a patient, such as a portion of a human hand 40 at which a finger has been severed as shown in FIG. 3. The tube fitting 32 may be attached to an end of a drain tube 50, so as to permit the tube 50 to convey fluids or other materials from the wound site that may be drawn from the wound site, through the opening 30 in the dressing 10 and into the drain tube, such as by application of a vacuum to the end of the drain tube remote from the end attached to the tube fitting 32. With the drain tube attached to the dressing, the release film 24 may be removed and then the dressing may be moved over the region of the hand 40, so the outer perimeter or border of the dressing generally surrounds the severed finger. The dressing 10 may then be moved toward the skin of the patient to cause the adhesive layer to contact and form a seal with the skin, and desirably enclose the wound site.

In one embodiment, the substrate of the dressing desirably may be substantially gas impermeable, so as to provide for efficient maintenance of a pressure differential between the region enclosed by the substrate and adhesive layer and the environment exterior to the enclosed region.

Figure 4:
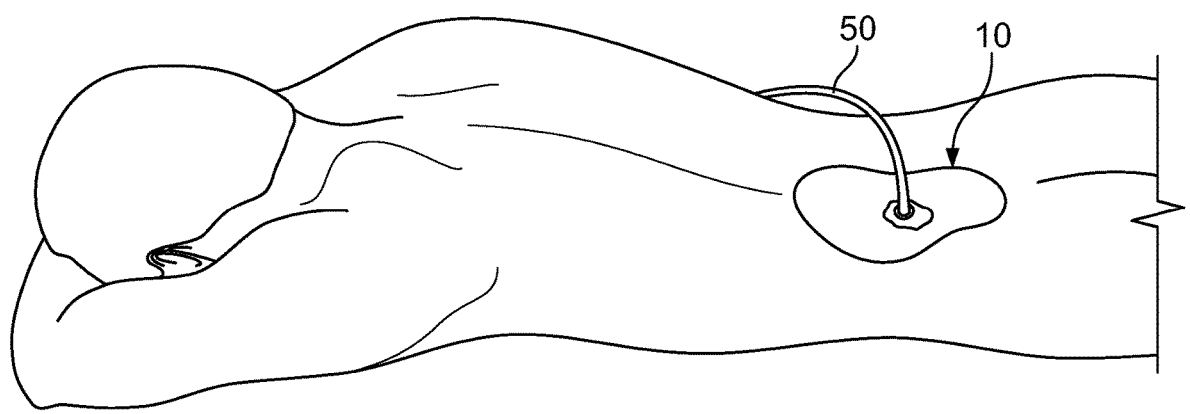
FIG. 4 is a diagrammatic view of a sacral wound site to which an exemplary embodiment of a self-sealing dressing is applied, in accordance with an aspect of the present invention.

Advantageously, the dressing 10 may be formed from materials that provide that the dressing is soft and conforming to the configuration of the wound site, such as the hand in the vicinity of the severed finger wound site, to provide a self-healing (self-sealing) adhesive interface at the adhesive layer. The cold flowing adhesive layer of the dressing may create a border seal for the dressing, to provide that the dressing may be self-healing with respect to the formation of leaks. For example, referring to FIG. 4, if the applied dressing 10 forms a leak along the adhesive border at a sacral wound site, at which movement is likely and which has a generally non-planar surface, based on formation of a wrinkle in the dressing when the patient moves, the leak may self-seal at the adhesive border under continued suction applied from a pump through the drain tube to the dressing 10.

In a desired embodiment, the dressing may be less than about 25 µm in thickness, and a seal between the dressing and the wound site may be maintained during repeated flexure and/or extension of the dressing, and if a leak is formed in the seal, the dressing may self-seal at the leak by application of suction. This self-sealing capability of the inventive dressing is in contrast to dressings of the prior art, which do not provide for self-sealing upon application of suction at the dressing, thereby compromising therapy and warranting action by an attending nurse.

In one embodiment, upon application of a vacuum at a wound site to which the dressing is applied, the dressing may permanently deform, resulting in minimal stresses being applied to the bond line between the dressing and the wound site.

In one embodiment, the substrate of the dressing may be sufficiently elastic, such as having an elasticity of about 10 $N/mm^2$ or an elasticity of about 5, 2 or 1 $N/mm^2$, to prevent undue stress along the seal formed by the adhesive layer of the dressing, during repeated flexure and extension of the dressing, such as may be caused by movement of the skin, stretching around the skin or flexure of the skin at the wound site.

In one embodiment, the adhesive layer may have sufficiently high peel strength, such that the adhesive layer, following application to form a seal to tissues at a wound site, does not become at least partially unadhered to the tissues during use. In one embodiment, the adhesive layer may be provided on the dressing so that the peel strength of the dressing is about 0.1-5 N/in, about 0.5-3 N/in or about 1-2 N/in.

In a further embodiment, the adhesive layer may be hydrophobic, such as a hydrocolloid adhesive, and maintain adhesive strength, even in the presence of moisture, so as to resist ingress of moisture.

In a further embodiment, referring again to FIG. 2, the substrate 12 of the dressing 10 may be sufficiently micro-textured and porous at the rear surface 16, such that the cold flow adhesive of the adhesive layer 18 may become intimately integrated with the substrate 12 during fabrication of the dressing to form an integrated layer region 70 at the rear surface 16 adjacent the adhesive layer 18. The integrated region 70 may provide that, when the dressing which is bonded to tissue at the wound site by the adhesive layer is removed from the wound site, the adhesive layer 18 may remain a part of the dressing laminate and not remain on the tissue when the dressing is removed from the wound site.

In a further embodiment, the substrate of the dressing may be a plastically deforming film, such as a cling wrap or polyethylene film, or stomahesive composition.

In an alternative embodiment, the substrate of the dressing may have a pseudo elastic stretchable region. The pseudo elastic stretchable region may have a pseudo elastic stretch characteristic that is maintained at linear strains of up to about 80%, up to about 40% or up to about 20%. In one embodiment, when the dressing is stretched beyond, for example, 20% stretch, the substrate of the dressing may behave pseudo elastically and not undergo significant permanent deformation. Thus, during use, the dressing may contort to accommodate movement, stretching, fluids and the like, but upon removal, the dressing may be sufficiently resilient to avoid tearing.

In another embodiment, the dressing may be easily removed by applying a warm compress near to or over the regions of the laminate with the adhesive, before pulling on the dressing to remove the dressing from the wound site.

In an exemplary method of fabrication of the inventive dressing, a substrate 12 may be provided with an opening 30 extending through the entirety of its thickness. The opening desirably has a width or diameter of about 20 mm or 40 mm. A layer of cold flowing adhesive 18 may be selectively deposited on the rear surface of the substrate, such as along the entirety of the perimeter of the rear surface. A release film may be applied over the adhesive layer 18, and optionally extend over the rear surface of the substrate. A layer of adhesive 34 may be applied at a portion of the top surface of the substrate surrounding the exposed portion of the opening, and a tube fitting 32 may be placed on the adhesive. The adhesive 34 may then be cured to attach the tube fitting to the substrate. Then, additional adhesive 34 may be applied at a portion of the top surface of the substrate surrounding the tube fitting, and a foam filled element, which is configured to surround the tube fitting, may be placed on the adhesive. The additional adhesive may then be cured to attach the foam filled element to the substrate. A lubricious coating layer may be deposited on the portions of the top surface of the substrate that are not covered by the tube fitting and the foamed element.

Exemplary self-sealing dressings that may be fabricated in accordance with the present invention are described below.

1) In one example, cold flow adhesive material may be coated onto a 25 µm thick polyurethane film, such that the resulting dry adhesive film has a thickness of 7 µm. For this dressing, it was found that the adhesive is reasonably aggressive to the skin, and the film is relatively durable in the presence of acetone and has exceptionally low rucking effects.

2) In another example, a cold flow adhesive material may be coated onto a 12 µm thick polyurethane film. The resulting dry adhesive of the dressing had a thickness of 7 µm. For this dressing, it was found that the adhesive is reasonably aggressive to the skin, and the film is relatively durable in the presence of acetone. In addition, the film has exceptionally low rucking effects. Furthermore, the dressing showed visibly superior conformance to microcracks on the surface of the skin relative to the dressing of Example 1.

3) In another example, cold flow adhesive material may be coated onto an 8 µm thick thermoplastic elastomer film having a shore hardness of about 30 A and an elongation to failure of about 800%. The resulting dry adhesive of the dressing had a thickness of about 7 µm. It was found that the adhesive is reasonably aggressive to the skin, and the film is relatively durable in the presence of acetone. The film also showed excellent rucking resistance. Furthermore, the film showed nearly ideal conformance to microcracks on the surface of the skin. In addition, the film conformed very well to the skin in regions where sufficient and repeated movement occurred during use.

The performance of the inventive self-sealing dressings was compared with prior art dressings with respect to MVTR, by performing examinations including a vacuum test on a concave feature; a rucking test, which included a test where the films are stroked with a brush for a predetermined number of strokes and the distance that the edge rolled up is measured; a comfort determination; and a clarity determination.

1) A prior art dressing ("Dressing 1") about 50 µm thick and including an adhesive was examined. The adhesive was estimated to be about 25 µm thick and appeared to be acrylic, and the substrate appeared to be low grade polyurethane. The following was observed. The Dressing 1 was reasonably elastic and the adhesive was very aggressive. The Dressing 1 was exceedingly painful to remove from skin with hair. The entire Dressing 1 dissolved very quickly in acetone. The Dressing 1 was sufficiently stiff so as to interfere with movement around joints. The Dressing 1 was also sufficiently stiff such that it could not easily be applied to convex surface features. In addition, the Dressing 1 was very prone to rucking and its use was painful as hairs at the wound site would get pulled into the roll during rucking.

2) A prior art dressing ("Dressing 2") about 50 µm thick was examined. Upon removal of the adhesive from the Dressing 2, the substrate was measured to be 25 µm thick. The Dressing 2 felt a little stiffer than Dressing 1 although it was reasonably elastic. It was observed that the Dressing 2 dissolved quickly in acetone with the adhesive dissolving much more quickly than the substrate, such that it was believed that the adhesive was an acrylate pressure sensitive adhesive and the substrate was a low grade polyurethane. The Dressing 2 was sufficiently stiff so as to interfere with movement around joints of a patient when applied to a wound site at the joints of a patient. Dressing 2 was also sufficiently stiff such that Dressing 2 could not easily be applied to a wound site having convex surface features. In addition, the Dressing 2 was very prone to rucking, and the removal process was painful as hairs of a patient would get pulled into the roll during rucking. Overall, Dressing 2 behaved very similarly to the Dressing 1 except that it felt stiffer.

3) A prior art dressing ("Dressing 3") about 90 µm thick was examined. The adhesive portion was about 35-40 µm thick, and the substrate was about 50 µm thick. It was found that the Dressing 3 was not very elastic, and it could not be readily repositioned. In other words, after application to skin at a wound site, when the Dressing 3 was broken away from the skin, the Dressing 3 could not be re-adhered to the skin. The entire Dressing 3 quickly dissolved in acetone. The adhesive appeared to be an acrylic pressure sensitive adhesive, and the substrate appeared to be a low grade polyurethane film. In addition, the adhesive was painfully aggressive and tore out hair upon removal of the Dressing 3 from the wound site. The Dressing 3 was sufficiently stiff so as to interfere with movement around joints. The Dressing 3 was also sufficiently stiff, such that it could not easily be applied to convex surface features. In addition, the Dressing 3 was very prone to rucking and pulled hairs into the roll during rucking, which contributed to the pain experienced during the removal process.

4) A prior art dressing ("Dressing 4") applied to a difficultly sized wound, for example, a sacral wound site, was examined. It was found that a leak formed along the edge of the Dressing 4, which apparently caused failure of the overall seal of the dressing.

Thus, the inventive dressing provides for improved performance over prior art dressings. In particular, the characteristics of the adhesive of the inventive dressing, such as the complex modulus, may have a higher mechanical loss factor than that of an acrylate pressure sensitive adhesive used in prior art dressings over typical usage temperatures and time frames. In addition, a leak formed along the edge of the inventive dressing applied to a wound site may self-seal under continued suction. Further, advantageously, the dressing of the present invention may avoid exposed portions, such as exposed edges of the substrate, catching on external objects; may provide that the edge portions of the dressing may be repositioned with relative ease if they are pulled up from the wound site; may provide that the adhesive is aggressive while simultaneously allowing ease of and relatively low pain removal; may substantially conform to wrinkles and cracks in the skin; may have sufficient elasticity, such that the dressing interface is not easily stressed during wear; and may remain conformed to the wound site in high movement areas of the body, such as over knuckles.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A wound dressing adapted for negative pressure wound therapy on the skin of a human comprising:
a substrate including elastomeric material; and
a cold flow adhesive layer directly coupled to the substrate, wherein the cold flow adhesive layer is a cold flow, shear thinning silicone gel adapted to adhere to the skin of the human to form a substantially gas impermeable seal between the cold flow, shear thinning silicone gel and the skin during application of negative pressure to a wound, wherein the cold flow, shear thinning silicone gel self-seals against leaks along an adhesive border of the wound dressing at the wound when suction is applied and is capable of being maintained during at least one of repeated flexure or extension of the dressing, wherein a maximum thickness of the combination of the substrate directly coupled to the cold flow adhesive layer is 25 µm; and
wherein the substrate has a thickness extending between a first side configured to face in a direction away from the skin of the human in use and a second side configured to confront the skin of the human in use, and an opening extending from the first side to the second side of the substrate, the opening being exposed at the first side of the substrate, wherein the second side of the substrate is directly coupled to the cold flow, shear thinning silicone gel.

2. The dressing of claim 1, wherein the cold flow, shear thinning silicone gel is adapted to maintain the substantially gas impermeable seal between the cold flow, shear thinning silicone gel and a portion of the skin of the human to which the cold flow, shear thinning silicone gel is adhered during movement of the portion of the skin.

3. The dressing of claim 2, wherein the portion of the skin is adjacent a site of the wound on the skin.

4. The dressing of claim 1, wherein the cold flow, shear thinning silicone gel is adapted to maintain the substantially gas impermeable seal between the cold flow, shear thinning silicone gel and a portion of the skin of the human to which the cold flow, shear thinning silicone gel is adhered, the portion of the skin having a predetermined surface characteristic.

5. The dressing of claim 4, wherein the predetermined surface characteristic is a plurality of microcracks.

6. The dressing of claim 1, wherein the substrate directly coupled to the cold flow adhesive layer of the dressing has a combined thickness of at least about 8µm.

7. The dressing of claim 1, wherein the substrate has a thickness about 1.2-1.9 times greater than a thickness of the cold flow adhesive layer.

8. The dressing of claim 1, wherein the substrate includes a predetermined portion having a predetermined elasticity characteristic.

9. The dressing of claim 1, wherein the substrate has a shore hardness of about 30A and an elongation to failure of about 800%.

10. The dressing of claim 1 further comprising:
a layer having lubricious characteristics covering a surface of the first side of the substrate.

11. The dressing of claim 1, wherein the substrate is sufficiently microtextured and porous at the second side.

12. The dressing of claim 1, wherein, when the dressing is adhered to the skin by the cold flow, shear thinning silicone gel, the dressing has a peel strength of about 0.1-2 N/in.

13. The dressing of claim 1, wherein the substrate includes a stretchable region in which linear strain is maintained up to about 80% at a maximum.

14. The dressing of claim 1, wherein the cold flow adhesive layer has a thickness of less than about 5µm.

15. A wound dressing comprising:
a substrate including elastomeric material;
a cold flow adhesive layer coupled to the substrate, wherein the cold flow adhesive layer is a cold flow, shear thinning silicone gel adapted to adhere to skin of a human to form a substantially gas impermeable seal between the cold flow, shear thinning silicone gel and the skin during application of negative pressure to a wound, wherein the cold flow, shear thinning silicone gel self-seals against leaks along an adhesive border of the wound dressing at the wound when suction is applied and is capable of being maintained during at least one of repeated flexure or extension of the dressing,
wherein a maximum thickness of the wound dressing is 25 µm;
wherein the substrate has a thickness extending between a first side configured to face in a direction away from the skin of the human in use and a second side configured to confront the skin of the human in use, and an opening is defined extending from the first side to the second side of the substrate, the opening being exposed at the first side of the substrate, wherein the second side of the substrate is directly coupled to the cold flow adhesive layer; and a layer having lubricious characteristics covering a surface of the first side of the substrate.

16. The dressing of claim 15, wherein the cold flow, shear thinning silicone gel and the substrate together at least partially comprise an integrated layer region adjacent to the cold flow, shear thinning silicone gel.

* * * * *